(12) United States Patent
McKinnon et al.

(10) Patent No.: US 6,227,668 B1
(45) Date of Patent: May 8, 2001

(54) VISUAL TEST USING COUNTER-PHASE CHROMATIC AND ACHROMATIC STIMULI

(75) Inventors: Stuart J. McKinnon, San Antonio, TX (US); Jeffrey L. Stewart, Greenwich, CT (US)

(73) Assignee: Visionrx Inc., Elmsford, NY (US)

( * ) Notice: Subject to any disclaimer, the term of this patent is extended or adjusted under 35 U.S.C. 154(b) by 0 days.

(21) Appl. No.: 09/628,792

(22) Filed: Jul. 29, 2000

Related U.S. Application Data

(62) Division of application No. 09/312,294, filed on May 14, 1999, now Pat. No. 6,068,377.

(51) Int. Cl.⁷ .................................................. A61B 3/02
(52) U.S. Cl. .............................................................. 351/222
(58) Field of Search .................................. 351/205, 211, 351/222, 246; 600/399, 401, 558; 128/898; 430/332, 333, 338, 339; 434/98, 102, 104

(56) References Cited

U.S. PATENT DOCUMENTS

| | | | |
|---|---|---|---|
| 5,026,286 | * 6/1991 | Hellwig | 434/98 |
| 5,053,320 | * 10/1991 | Robillard | 430/339 |

\* cited by examiner

*Primary Examiner*—George Manuel
(74) *Attorney, Agent, or Firm*—J. De La Rosa

(57) ABSTRACT

A novel psychophysical visual test based on the visual response of the eye to alternating chromatic complementary colors or achromatic grays of varying saturation, luminance and/or contrast is proposed for the early detection of glaucoma, and other diseases. In one embodiment, although the luminance level remains constant, the visual stimulus alternates between two complementary or counter phase colors, preferably against a gray background at about 40 times a sec, for example, between blue and yellow. When the colors are alternated in this manner, the visual stimulus appears white or gray to an observer, instead of either blue or yellow. As the saturation is reduced, however, the alternating colors appear grayer, and then eventually cannot be perceived. Persons suffering from glaucoma and other diseases, however, find it more difficult than normal people to distinguish the visual stimulus as the saturation and/or luminance is reduced. Observation thresholds for the visual stimulus can be measured by reducing the saturation of the alternating colors until the visual stimulus disappears against the gray background, and used beneficially to detect for the presence of glaucoma and other diseases. Alternatively, however, the luminance of the colors can be varied as the saturation is held constant, or varied together. In another embodiment, an achromatic stimulus consisting of black, white and grays may be used. In this latter instance, the visual stimulus consists of a circular patch or spot alternating preferably between black and white.

55 Claims, 5 Drawing Sheets

VISUAL TEST USING COUNTER-PHASE CHROMATIC AND ACHROMATIC STIMULI

CROSS-REFERENCE TO RELATED APPLICATION

This application is a Divisional of U.S. Ser. No. 09/312,294, entitled "Visual Test Utilizing Color Frequency Doubling" filed May 14, 1999, which issued as U.S. Pat. No. 6,068,377 on May 30, 2000, and which is incorporated herein by reference.

TECHNICAL FIELD

The present invention relates to visual test systems, and more particularly, to visual test systems used for the early detection of retinal diseases and eye disorders, particularly glaucoma.

BACKGROUND OF THE INVENTION

Glaucoma is one of the leading causes of blindness, resulting from the loss of a particular type of retinal cells, more specifically, retinal ganglion cells (RGC). Axons of the ganglion cells project out of the eye to form the optic nerve. With the loss of ganglion cells, the optic nerve which connects the retina to the brain is gradually destroyed, and results in blindness if the disease is not treated early enough.

Although typical signs of glaucoma include a scotoma as well as a "cupping" of the optical disc, by the time such signs are detected, treatment is unlikely to be successful. While glaucoma is typically associated with an elevation in a patient's intraocular pressure, testing for such an elevation is generally unreliable. This is so, since an elevated intraocular pressure typically occurs transiently in the morning and evening, or may not even be exhibited by some patients.

As such, an evaluation of the patient's visual field has long been the method used for the clinical diagnosis of glaucoma, as well as other pathologies. For example, in so-called "white-on-white" perimetry, a white test object of varying contrast is displayed against a white background at different points in the patient's visual field. The characteristic locations where the test object is undetected for a particular contrast allow clinicians not only to diagnose, but also to determine the severity of the glaucoma. A drawback, however, to this approach is its lack of sensitivity, typically detecting glaucoma only after 30–50% of retinal ganglion cells have been lost or destroyed.

Efforts to improve the sensitivity of the above latter approach have focused on the physiology of retinal ganglion cells. For example, in "short-wave" automated perimetry (SWAP), a blue rather than a white test object is displayed within the patient's visual field, and against a yellow background. The characteristic locations where the test object is undetected for a particular contrast are used to effectively screen patients for glaucoma damage.

Recently, another approach using the phenomenon of so-called "frequency doubling" has also been used for the early detection of glaucoma. See, for example, U.S. Pat. No. 5,065,767, which is incorporated herein by reference. As shown in FIG. 1, in this latter approach, a sinusoidal grating pattern 10 consisting of light and dark bars or striations 20, 30, respectively, is modulated at a temporal frequency between 10 and 50 Hz. That is, the bars are contrast modulated in a sinusoidal fashion from white through gray to black at about 10 to 50 times a sec. At such frequencies, typically about 40 Hz, the grating pattern is perceived by patients to have double the spatial frequency. For a discussion on this phenomenon, see, for example, D. H. Kelly, "Frequency Doubling In Visual Response," *J. Opt. Soc. Am.*, 56:1628–33 (1966); and D. H. Kelly, "Nonlinear Visual Responses To Flickering Sinusoidal Gratings," *J. Opt. Soc. Am.* 1051–55 (1981).

Patients suffering from glaucoma typically require twice the contrast level between the white and black bars before observing the above frequency doubling phenomenon. This phenomenon is now understood to be a non-linear visual response of the eye. Importantly, this difference in visual response between patients with normal vision and those suffering from glaucoma is used to detect the disease at an earlier stage.

In the above referenced related issued patent, still yet another psychophysical visual test was proposed for testing a person for glaucoma and other diseases which appears to have greater sensitivity. This visual test was based on the discovery that the frequency doubling phenomenon noted herein above was also discovered to be produced by color visual stimuli. More specifically, it was discovered that a visual stimulus consisting of a grating pattern with alternating colors also produced the frequency doubling phenomenon. That is, the colors were preferably of the same luminance or intensity level, i.e., isoluminent, but each grating alternates from one color to another, such as from blue to yellow, and vice a versa.

More specifically, there is shown in FIG. 2 a color visual stimulus 40 consisting of two circular gratings 50, 60, here having two spatial cycles. Although the luminance level remains constant, the color of each grating alternates preferably between two colors at a frequency $f_s$ of about 10–50 times a sec. That is, each grating switches back and forth between the two colors at a desired frequency, here the complementary color pair of blue and yellow. At any instance in time, however, the "saturation" of each color varies sinusoidally radially inward, ranging from a maximum to a minimum.

When the colors in visual stimulus 40 are alternated at a frequency between 10–50 Hz, the frequency doubling phenomenon causes four cycles to be perceived, instead of two, if the visual stimulus is observed. Persons suffering from eye disorders, such as glaucoma, however, find it more difficult than normal people to observe this frequency-doubled stimulus. Observation thresholds for this stimulus can be measured by reducing the "saturation" levels of the colors until the visual stimulus disappears. Persons suffering from glaucoma and other diseases will be unable to detect the visual stimulus as the saturation levels are reduced.

Although the above latter color frequency doubling visual test performs well, it would still be desirable to have an alternative visual test which may have a greater sensitivity, so as to detect eye diseases, particularly glaucoma, at its earliest possible stage.

SUMMARY OF THE INVENTION

A novel psychophysical visual effect based on the discovery that the visual response of the eye to alternating counter-phase chromatic stimuli (complementary colors) as well as achromatic stimuli (black, white and grays) is proposed for the early detection of glaucoma, and other eye diseases.

In one embodiment, a visual stimulus consisting of a circular object, such as a patch or spot, is displayed with alternating colors, preferably against a gray background. Although the luminance level remains constant, the visual stimulus preferably alternates between two complementary or counter phase colors at a frequency $f_s$ of about 10–50 times a sec, preferably 40. In other words, the visual stimulus switches back and forth between the two colors, for example, blue and yellow, at the desired frequency. Alternatively, however, the luminance of the colors can be varied as the saturation is held constant.

When the colors are alternated at a frequency between 10–50 Hz, it appears white (or gray) to the observer, instead of either blue or yellow. As the saturation and/or luminance is reduced, however, the alternating colors appear grayer, and then eventually cannot be perceived. Persons suffering from retinal diseases and other eye disorders, such as glaucoma, however, find it more difficult than normal people to distinguish the visual stimulus as the saturation and/or luminance is reduced. Observation thresholds for the visual stimulus can be measured by reducing the saturation S and/or luminance L between the alternating colors until the visual stimulus disappears, and used beneficially to detect for the presence of glaucoma, and other eye diseases.

One method to determine the threshold value or level at which the visual stimulus is not observed is a modified binary staircase algorithm that involves (i) reducing the saturation (or luminance) by one-half of the previous value until no visual stimulus is observed; and then (ii) increasing the saturation (or luminance) in predetermined incremental steps until the visual stimulus is again perceived. Taking the average value then precisely determines the threshold level.

To diagnose more accurately for glaucoma and other diseases, however, a visual mapping of the patient's visual field or peripheral vision is more preferable. Characteristic locations where the visual stimulus is undetected may allow clinicians, for example, not only to diagnose, but also to determine the severity of the glaucoma. Accordingly, it is preferable to record the patient's response to the visual stimulus as the stimulus is displayed throughout the patient's visual field. To perform such a visual perimetry, a computer may be programmed to display the visual stimulus at various locations on a color monitor, corresponding to different visual field locations. Importantly, the colors of the visual stimulus alternate, for example, between yellow and blue, at a desired temporal frequency. In addition to displaying the visual stimulus, the computer monitors the patient's response to the stimulus as the saturation (and/or luminance) is varied, which response may be entered by pressing a button, such as on a computer mouse. In this manner, a visual mapping of the patient's retina is then provided.

In another embodiment, an achromatic stimulus consisting of black, white and grays may be used. In this latter instance, the visual stimulus consists of a circular patch or spot alternating preferably between black and white. As the contrast between the black and white is reduced, it appears grayer, and then eventually cannot be perceived. Similarly, persons suffering from retinal diseases and other eye disorders, such as glaucoma, find it more difficult than normal people to distinguish the visual stimulus as the contrast is reduced. Observation thresholds for the visual stimulus likewise can be measured by reducing the contrast between the black and white until the visual stimulus disappears.

BRIEF DESCRIPTION OF THE DRAWINGS

The features and advantages of the present invention will become more readily apparent from the following detailed description of the invention in which like elements are labeled similarly and in which.

DETAILED DESCRIPTION

In accordance with the principles of the invention, a novel psychophysical test utilizing alternating counter-phase chromatic colors or achromatic grays is proposed which may be more sensitive to the loss of retinal ganglion cells than conventional visual field perimetric techniques. The present invention is based on the discovery that the visual response of the eye to alternating counter-phase colors or achromatic grays of varying saturation, luminance and/or contrast may be used for the early detection of glaucoma and other diseases. It is believed that this visual response is due to the subset of $M_y$ ganglion cells present in the retina responsible also for producing the frequency doubling phenomenon to alternating colors in a grating pattern.

Figure 1:
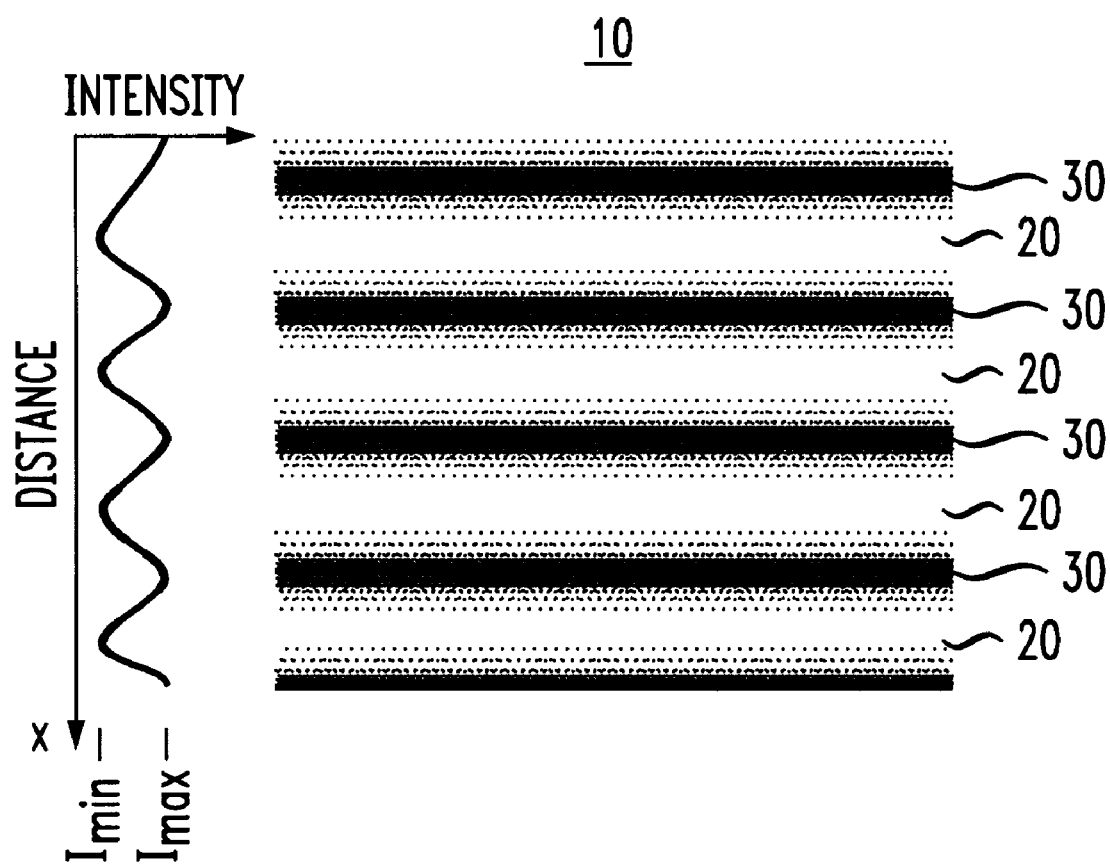
FIG. 1 depicts a sinusoidal grating of the prior art consisting of white to black bars which when modulated at a temporal frequency of 10–50 Hz is observed as having double the spatial frequency.
Figure 2:
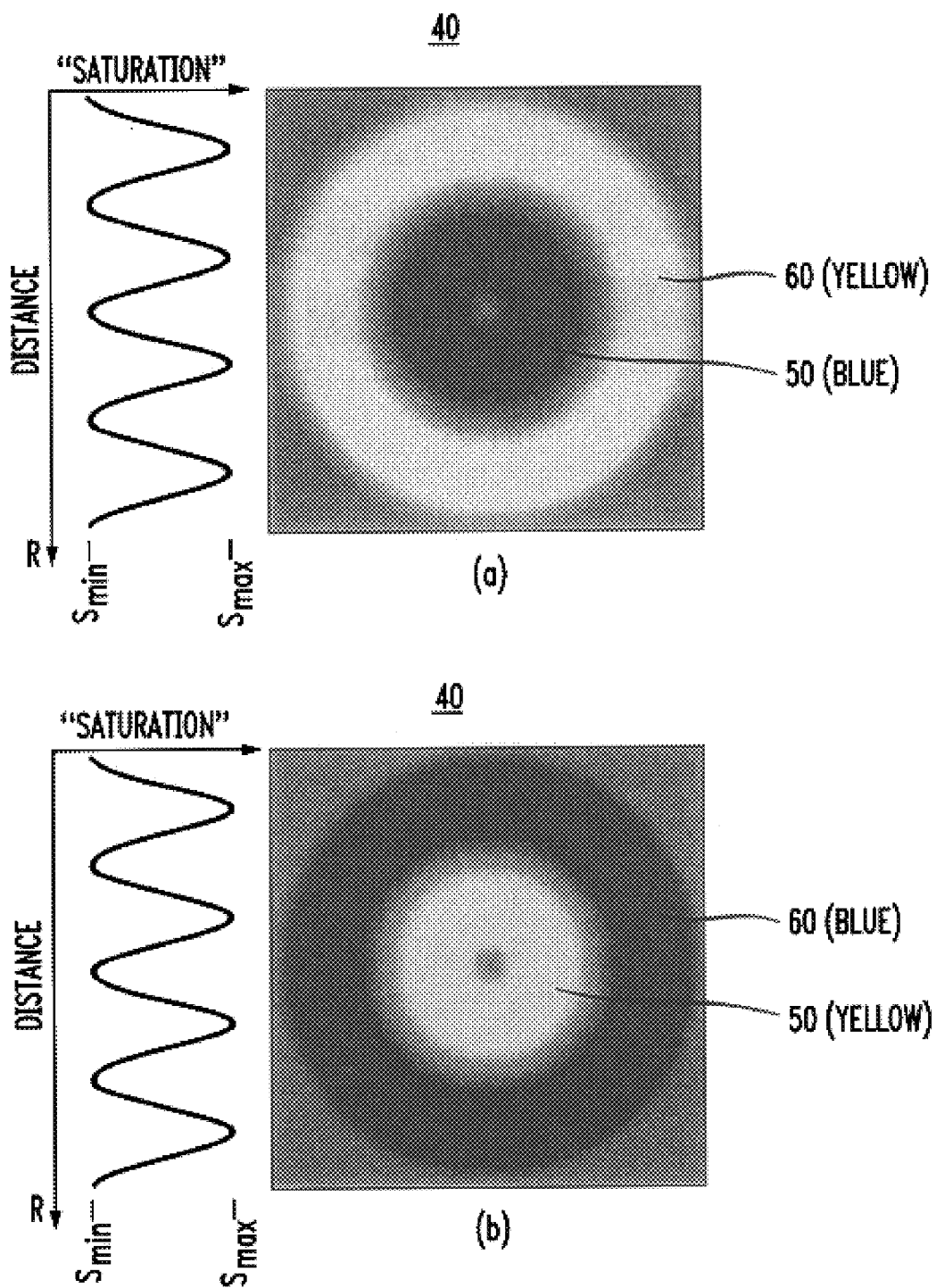
FIG. 2 depicts a color visual stimulus consisting of isoluminent circular color gratings, one blue and one yellow.
Figure 3:
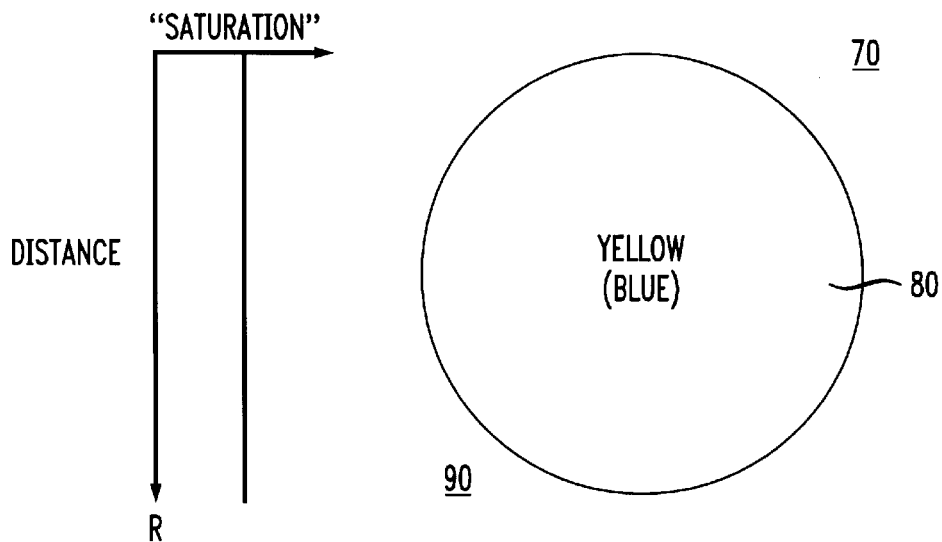
FIG. 3 depicts a visual stimulus consisting of a circular object which alternates between two complementary or counter-phase colors in accordance with the principles of the present invention.

Referring to FIG. 3, there is shown one embodiment of a visual stimulus 70 consisting of a circular object 80 having alternating complementary or counter-phase colors (chromatic stimulus), which are displayed preferably against a gray background 90. Of course, different background colors may also be used, if desired, depending on the application. Although the luminance level remains preferably constant, visual stimulus 70 alternates between the two complementary or counter phase colors at a frequency $f_s$ of about 10–50 Hz, preferably 40. In other words, the visual stimulus switches back and forth between the two colors at the desired frequency, here the complementary color pair of blue and yellow.

Figure 4:
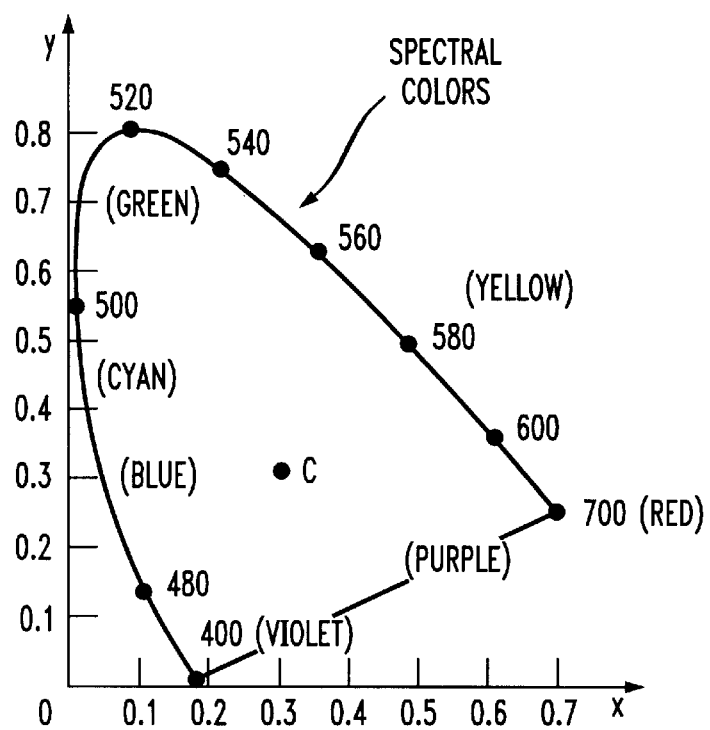
FIG. 4 depicts the CIE chromaticity diagram.

The complementary colors are preferably of the same luminance or intensity level, i.e., isoluminent, and when combined produce white light. Examples of complementary color pairs are red and cyan, green and magenta, and blue and yellow. Other complementary colors may be obtained by reference, for example, to the CIE chromaticity diagram shown in FIG. 4. Points along the curve are the "pure" colors, with point C in the diagram corresponding to white. Complementary colors are represented on this chromaticity diagram as two color pairs situated on opposite sides of C and connected with a straight line. Similarly, in other color system models, the complementary colors are 180° degrees apart, such as in the RGB, HSV and HSL color models, among others.

The "saturation" or "purity" of each color throughout visual stimulus 70 is substantially uniform. Throughout this specification, the term saturation S or purity refers to the amount of dilution of the pure color or hue with neutral gray of the same luminance, as commonly used in the field of colorimetry. The saturation S varies from 0 to 1, and has a maximum purity at S=1. In some chromaticity diagrams or color systems, this latter characteristic of color is known as chroma.

When the colors in visual stimulus 70 are alternated at a frequency between 10–50 Hz, it appears white (or gray) to the observer, instead of either blue or yellow. As the saturation is reduced from its maximum (S=1), the alternating colors appear to get grayer, and then eventually cannot be perceived against gray background 90. Persons suffering from glaucoma and other diseases, however, find it more difficult than normal people to distinguish visual stimulus 70 against gray background 90 as the saturation is reduced. Observation thresholds for visual stimulus 70 can be measured by reducing the saturation S of the colors until the visual stimulus disappears against gray background 90. This is based on the reasoning that a diffuse loss in the $M_y$ cells at the onset of glaucoma and other diseases would raise the observation threshold, and hence can be used to screen patients for such diseases, such as glaucoma.

Alternatively, however, the luminance L of the colors can be varied while the saturation S is held constant. The term luminance L refers to the brightness or the perceived intensity of the colors. Similarly, visual stimulus 70 consists of circular object 80 alternating between the two complementary or counter-phase colors. As the luminance L of the colors is reduced, however, the alternating colors again appear grayer, and then eventually cannot be perceived. Similarly, persons suffering from retinal diseases and other eye disorders, such as glaucoma, however, find it more difficult than normal people to distinguish the visual stimulus as the luminance is reduced. Observation thresholds for the visual stimulus likewise can be measured by reducing the luminance L of the alternating colors until the visual stimulus disappears. Of course, both the luminance and saturation may be varied together, but may make determining the observation threshold more difficult.

As such, it should be clearly understood that although the invention is discussed below primarily in terms of varying the saturation, other alternative embodiments include those where the observation threshold is based on varying the luminance L instead of the saturation S. Furthermore, however, both the saturation and luminance can be varied at the same time to produce the same visual effect, as discussed above herein, and included within the scope of the invention.

Preferably, visual stimulus 70 is viewed monocularly from a distance at which it subtends about 0.4 degrees of visual angle, which can be readily adjusted by judiciously selecting the dimensions of the visual stimulus, as well as the distance from which the stimulus is observed.

Although other geometrical shapes may also be used for the visual stimulus, a circular geometrical shape is preferable inasmuch as data collected using such visual stimuli may be readily compared, for example, to perimetry techniques that employ circular test objects, such as Humphrey, Inrerzeag, and Dicon perimeters, among others.

In view of the above, one visual technique to test a person for glaucoma as well as other diseases comprises displaying visual stimulus 70 to the person against gray background 90, with its color alternating, for example, between blue and yellow at a temporal frequency or rate of about 10–50 Hz. The saturation S of the colors is such that the person preferably observes a white circular object against gray background 90, although a light gray is acceptable. Persons suffering from the loss of PC ganglion cells as a result of glaucoma, as well as other pathologies, will be unable to detect visual stimulus 70 against this gray background 90 as the saturation is reduced. Therefore, the present technique further comprises reducing the saturation S of the colors below a threshold level where visual stimulus 70 is no longer observed by the person. Comparing the threshold level against those of persons with normal vision should enable a clinician to screen persons with glaucoma, as well as other pathologies.

It should be clearly understood that as the saturation S is reduced below the threshold level, no visual stimulus whatsoever is observed. That is, the person observes visual stimulus 70 getting grayer until no visual stimulus whatsoever is observed.

Inasmuch as the saturation is used to detect for glaucoma and other diseases, it is important to accurately determine the threshold value or level at which visual stimulus 70 is not observed. For this purpose, a modified binary staircase algorithm may be used, and involves (i) reducing the saturation S by one-half of the previous value until the visual stimulus is not observed; and then (ii) increasing the saturation in predetermined incremental steps until the visual stimulus is perceived so as to determine precisely the threshold level. The average threshold is then used as the threshold saturation at which the person no longer observes visual stimulus 70. Alternatively, the saturation S may be first increased by one-half, and then decreased in predetermined increments.

Note that the use of blue and yellow colors have the advantage of not only testing for the loss of $M_y$ ganglion cells, but also for blue-yellow PC ganglion cells, which are believed to be lost at a significantly higher rate than red-green PC cells at the onset of glaucoma. Although PC ganglion cells respond slowly to luminance changes, their response is also believed to improve greatly with a color stimulus, such as visual stimulus 70. Moreover, blue-yellow ganglion cells cover a larger receptive field on the retina. As such, the visual test of the present invention should have greater sensitivity than other visual field test techniques.

Thus, based on our understanding of the physiology of the retina, it is anticipated that persons having normal vision and those suffering from glaucoma and other diseases will have different visual responses to the above visual stimulus 70, with glaucoma patients requiring a greater degree of saturation or purity before observing visual stimulus 70 against gray background 90.

To diagnose more accurately for glaucoma and other diseases, however, it is particularly important to obtain a visual mapping of the patient's visual field or peripheral vision. Determining where the visual stimulus is undetected allows clinicians not only to diagnose, but also to determine the severity of the glaucoma and other visual field losses. Accordingly, it is preferable to record the patient's response to visual stimulus 70 as the stimulus is displayed throughout the patient's visual field, using one eye at a time. In particular, the patient's central vision should be fixated on a single point while visual stimulus 70 is displayed in a random fashion at other points within the patient's visual field. To perform such a visual field perimetry, either static or kinetic, a patient preferably will be required to move a cursor towards a fixation target which is displayed on a computer monitor, as disclosed more fully in copending application Ser. No. 09/604,571 entitled "Method For Establishing Fixation In Visual Field Perimetry," which is incorporated herein by reference. Alternatively, the moving fixation technique disclosed in U.S. Pat. No. 5,565,949 may be employed, which is incorporated herein by reference. Other fixation techniques, of course, may be used, such as so-called "blind spot monitoring," among others.

Once having established fixation, visual stimulus 70 will be displayed in a random fashion at each of the desired points within the patient's visual field, and the patient confirms detection of the stimulus by pressing a switch, e.g., a mouse button, or orally, using voice recognition. Note that visual stimulus 70 may be displayed at either preprogrammed or manually selected locations within the patient's visual field, depending on the type of testing to be performed.

Upon responding to visual stimulus 70, the cursor may then be automatically positioned outside the fixation target for the patient again to move the cursor towards the fixation target before displaying the next stimulus at another visual field location. Using the above described binary staircase algorithm, visual stimulus 70 is displayed at the same location, but at different times until the saturation S reaches the threshold level where the visual stimulus is not seen. Note that in so-called "suprathreshold" testing or screening, however, the visual stimulus is only shown once at each visual field location. In this latter case, visual stimuli are displayed with a predetermined saturation level, such as the level expected for persons with normal vision.

In order to ensure, however, that the results of this novel visual perimetry can be readily compared to the accepted standards of automated perimetry, it is preferable to display visual stimulus 70 at each of the 54 grid points of the standard 24-2 test pattern wherein each grid point is spaced about at 6 degrees of visual field. The number of stimuli, their locations, and color saturation, however, may be chosen in different manners, depending on the test strategy that is to be employed. For example, in the above mentioned "suprathreshold" testing a lower number of visual field locations may be used to reduce the test time.

Also, to ensure reliability in the patient's response, false-positive and false-negative visual stimuli may be presented to the patient, such techniques being well known to those skilled in the art. In the former case, a blank stimulus is displayed, whereas in the latter a stimulus is displayed having a saturation higher than the one previously displayed at the same visual field location.

Figure 5:
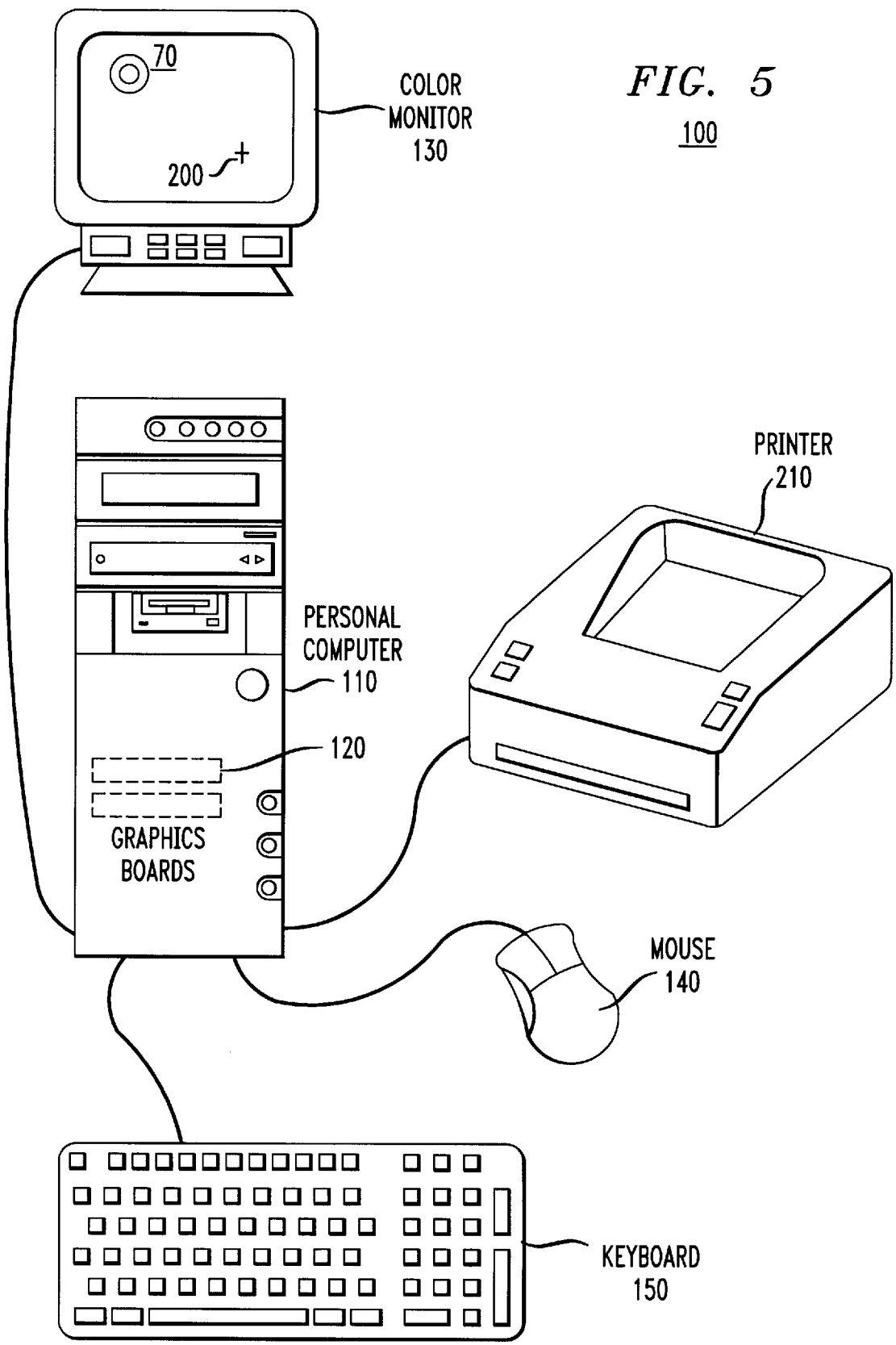
FIG. 5 depicts a simplified block diagram of a visual test system which may be employed to perform visual perimetry in accordance with the principles of the invention.

Inasmuch as the present invention also encompasses an apparatus for performing the above inventive visual test, shown in FIG. 5 is a simplified block diagram of a visual perimeter 100 in accordance with the principles of the invention. Visual test system 100 comprises a computer 110, such as a personal computer (PC) running under Windows. Computer 110 includes conventional graphics boards 120 which may be readily programmed to display visual stimulus 70 against gray background 90 at various locations on a color monitor 130 corresponding to different visual field locations. Importantly, visual stimulus 70 alternates between yellow and blue at a frequency of 10–50 Hz. In addition to displaying visual stimulus 70, computer 110 monitors the patient's response which is entered by pressing a button, such as on a computer mouse 140, or alternatively entered by other means such as voice recognition.

Figure 6:
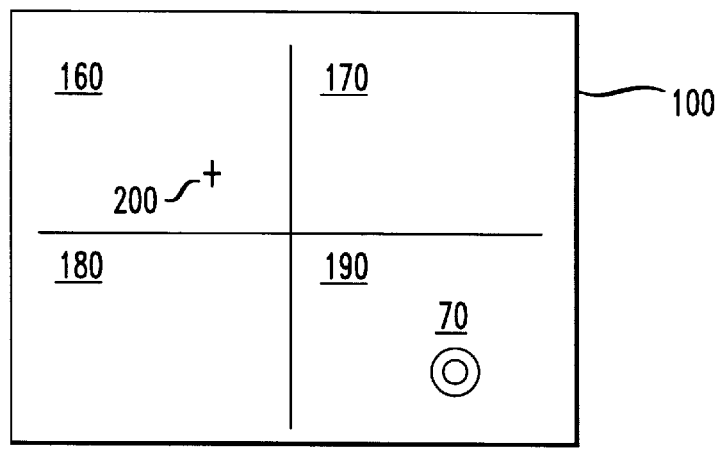
FIG. 6 depicts the screen of the color monitor of FIG. 5, which has been broken into four quadrants.

In this preferred embodiment, the patient views color monitor 130 at a predetermined distance for the stimulus to subtend a predetermined angle. Of course, the patient views the stimulus monocularly, with each eye tested separately. An operator may be seated at or near computer 110 for controlling the test parameters via a keyboard 150, or the testing may be fully automated. Referring to FIG. 6, the perimeter corresponding to the screen of color monitor 130 is preferably broken into four quadrants 160, 170, 180, 190, with a fixation target 200 moved into the outer corner of each of the four quadrants to test points in the patient's visual field that are farther from the center. In this latter manner, the effective size of the screen is increased four-fold, allowing visual field testing to be performed for angles which would have required displays of much larger size.

Recall that visual stimuli 70 can be displayed either at preprogrammed or manually selected locations within the patient's visual field. In accordance with the above test algorithm, computer 110 accordingly adjusts the saturation of the colors to precisely determine the threshold level at which visual stimulus 70 is no longer observed. Glaucoma sufferers will typically require a much higher saturation level. Recording the patient's response to the visual stimuli provides a visual mapping of the patient's visual field, not unlike conventional perimetry.

In another embodiment of the present invention, visual stimulus 70 instead is an achromatic stimulus, consisting of alternating achromatic grays, preferably black and white. Contrastingly, in this latter embodiment, visual stimulus 70 consists of a circular object alternating between black and white. Similarly, as the contrast between the alternating black and white stimulus is reduced, the alternating black and white appear grayer, and then eventually cannot be perceived. Persons suffering from retinal diseases and other eye disorders, such as glaucoma, again find it more difficult than normal people to distinguish the visual stimulus as the contrast is reduced. Modified binary staircase algorithms as discussed herein above may be used to accurately determine the threshold level at which visual stimulus 70 is not observed, except that it is contrast which is varied. Also, visual mapping, including the use of fixation techniques, may also be used to diagnose more accurately for eye diseases, particularly glaucoma.

Software to implement the above described visual field perimetry therefore includes displaying and varying the saturation, luminance and/or contrast of the stimulus, monitoring the patient's fixation, recording the patient's response to the stimuli, and mapping the visual field on the basis of the patient's responses. Such software is readily capable of implementation by those skilled in the art who have been equipped with the understanding of the operation of the present invention as set forth herein, and may be written in C++, or any other programming language.

In addition to printing the test data on a printer 210 for each patient, either in graphical or text format, such test data may be saved on hard disk, recalled for later use, imported into a database for statistical analysis, and/or transmitted to a remote location.

Although the present invention has been realized and discussed in terms of displaying visual stimulus 70 on color monitor 130, it is to be clearly understood that the present invention may have equally employed other types of displays, such as projection screens, LCDs, heads up displays (HUDs), total immersion displays, and the like. Also, the present invention may employ the multi-functional visual testing instrument of U.S. Pat. No. 6,045,227, which is incorporated herein by reference.

Figure 7:
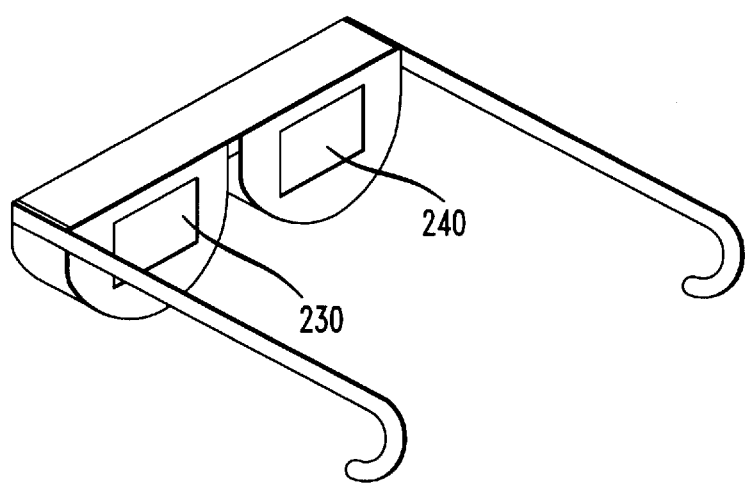
FIG. 7 depicts a close proximity display in the form of virtual reality glasses, which may be used by a patient to observe the visual stimulus of FIG. 3.

Still further, as shown in FIG. 7, total immersion displays, such as close proximity displays in the form of virtual reality glasses 220, may be used to display visual stimulus 70 to the patient, which advantageously may contain two independent displays 230, 240. See, for example, U.S. Pat. Nos. 5,565,949; and 5,737,060, which are incorporated herein by reference. In this latter case, both eyes can be tested at once by displaying visual stimulus 70 to each eye independently. That is, visual stimulus 70 is first displayed to right eye display 240 of virtual reality glasses 220, and then to left eye display 230, without the patient being able to distinguish which eye is being tested. Note that in this latter instance, the patient will view the fixation target binocularly. Similarly, testing may then be performed as discussed herein above.

It should be clearly understood that the embodiments herein are merely illustrative of the principles of the invention. Various modifications may be made by those skilled in the art which will embody the principles of the invention and fall within the spirit and the scope thereof. Furthermore, although the invention has been discussed in terms of its applicability particularly to glaucoma, the present invention also has utility in testing for other eye diseases.

What is claimed is:

1. A method of identifying those persons possibly suffering from eye disorders, including glaucoma, comprising the steps of:

displaying to a person a visual stimulus, said visual stimulus alternating from a first to a second color at a desired temporal frequency, with the saturation and/or luminance of the colors being such that the person perceives the visual stimulus as being white or gray;

reducing the saturation and/or luminance of said first and second colors until the person no longer perceives the visual stimulus; and comparing the saturation and/or luminance of said first and second colors at which the person no longer perceives the visual stimulus with the saturation or luminance at which a person with normal vision no longer perceives the visual stimulus.

2. The method of claim 1 wherein said visual stimulus is displayed against a gray background.

3. The method of claim 1 wherein the first and second colors are isoluminent.

4. The method of claim 1 wherein the visual stimulus is in the form of a circular object.

5. The method of claim 1 wherein the first and second colors are complementary colors.

6. The method of claim 5 wherein the complementary colors are blue and yellow.

7. The method of claim 1 further comprising positioning the person in front of a display on which the visual stimulus is displayed at various locations corresponding to locations within the person's visual field.

8. The method of claim 1 wherein the step of reducing the saturation and/or luminance comprises reducing the saturation or luminance by a predetermined fraction of the previous value until the person no longer perceives the visual stimulus, and then increasing the saturation and/or luminance in predetermined incremental steps until the person again perceives the visual stimulus.

9. The method of claim 1 wherein the step of displaying the visual stimulus to the person comprises displaying the visual stimulus at predetermined locations within the person's visual field.

10. The method of claim 1 further comprising the step of using a fixation target to fixate the person's central vision.

11. The method of claim 1 further comprising the step of monitoring the person's fixation.

12. The method of claim 10 wherein the fixation target is displayed at different locations within the person's visual field.

13. A method of identifying those persons possibly suffering from eye disorders, including glaucoma, comprising the steps of:

displaying to a person a visual stimulus, said visual stimulus alternating from black to white at a desired temporal frequency, with the contrast between the black and white being such that the person perceives the visual stimulus as being gray;

reducing the contrast between the black and white until the person no longer perceives the visual stimulus; and comparing the contrast at which the person no longer perceives the visual stimulus with the contrast at which a person with normal vision no longer perceives the visual stimulus.

14. The method of claim 13 wherein said visual stimulus is displayed against a gray background.

15. The method of claim 13 wherein the visual stimulus is in the form of a circular object.

16. The method of claim 13 further comprising positioning the person in front of a display on which the visual stimulus is displayed at various locations corresponding to locations within the person's visual field.

17. The method of claim 13 wherein the step of reducing the contrast comprises reducing the contrast by a predetermined fraction of the previous value until the person no longer perceives the visual stimulus, and then increasing the contrast in predetermined incremental steps until the person again perceives the visual stimulus.

18. The method of claim 13 wherein the step of displaying the visual stimulus to the person comprises displaying the visual stimulus at predetermined locations within the person's visual field.

19. The method of claim 13 further comprising the step of using a fixation target to fixate the person's central vision.

20. The method of claim 13 further comprising the step of monitoring the person's fixation.

21. The method of claim 19 wherein the fixation target is displayed at different locations within the person's visual field.

22. A method for detecting the loss of function of the retina of a person comprising the steps of:

positioning the person in front of a display;

displaying on the display a visual stimulus alternating between two chromatic colors or achromatic grays at a predetermined temporal frequency, the saturation, luminance or contrast of the colors or grays sufficient for the person to perceive the visual stimulus;

varying the saturation, luminance or contrast of the colors or grays;

recording as an observation threshold the saturation, luminance or contrast at which the person no longer perceives the visual stimulus; and comparing the observation threshold with that of a person with normal vision, wherein a substantially higher than normal observation threshold is indicative of the loss of retinal function.

23. The method of claim 22 wherein said visual stimulus is displayed against a gray background.

24. The method of claim 22 wherein said visual stimulus is displayed against a color background.

25. The method of claim 22 wherein the chromatic colors are a complementary color pair.

26. The method of claim 25 wherein the complementary color pair is blue and yellow.

27. The method of claim 22 wherein the achromatic grays are white and black.

28. The method of claim 22 wherein the step of varying the saturation, luminance or contrast comprises reducing the saturation, luminance or contrast by a predetermined fraction of the previous value until the person no longer perceives the visual stimulus, and then increasing the saturation, luminance or contrast in predetermined incremental steps until the person again perceives the visual stimulus.

29. The method of claim 22 wherein the step of displaying the visual stimulus to the person comprises displaying the visual stimulus at predetermined locations within the person's visual field.

30. The method of claim 22 further comprising the step of using a fixation target to fixate the person's central vision.

31. The method of claim 22 further comprising the step of monitoring the person's fixation.

32. The method of claim 30 wherein the fixation target is displayed at different locations within the person's visual field.

33. A system for identifying those persons possibly suffering from glaucoma and other eye diseases, comprising:
   a display;
   means for displaying on said display a visual stimulus, said visual stimulus consisting of colors alternating from a first to a second color at a desired temporal frequency, with the saturation and/or luminance level of the colors being substantially uniform within the visual stimulus such that a person perceives the visual stimulus as being white or gray;
   means for reducing the saturation and/or luminance level of said colors until the person no longer perceives the visual stimulus; and
   means for comparing the saturation and/or luminance level of said colors at which the person no longer perceives the visual stimulus with the saturation and/or luminance level at which a person with normal vision no longer perceives the visual stimulus.

34. The system of claim 33 wherein said visual stimulus is displayed against a gray background.

35. The system of claim 33 wherein the first and second colors are isoluminent.

36. The system of claim 35 further comprising means for recording the person's response to the visual stimulus.

37. The system of claim 33 wherein the first and second colors are complementary colors.

38. The system of claim 37 wherein the complementary colors are blue and yellow.

39. The system of claim 33 wherein the saturation and/or luminance level of the colors is reduced by a predetermined fraction of the previous value until the person no longer perceives the visual stimulus, and then is increased in predetermined incremental steps until the person again perceives the visual stimulus.

40. The system of claim 33 wherein the visual stimulus is displayed at predetermined locations within the person's visual field.

41. The system of claim 33 further including means for fixating the person's central vision.

42. The system of claim 41 wherein said means for fixating includes a fixation target.

43. The system of claim 42 wherein said fixation target is displayed at different locations within the person's visual field.

44. The system of claim 41 wherein said means for fixating includes means for monitoring the person's fixation.

45. The system of claim 33 wherein said means for displaying includes a computer.

46. A system for identifying those persons possibly suffering from glaucoma and other eye diseases, comprising:
   a display;
   means for displaying on said display a visual stimulus, said visual stimulus alternating between white and black at a desired temporal frequency, with the contrast therebetween sufficient for a person to perceive the visual stimulus;
   means for reducing the contrast between the black and white until the person no longer perceives the visual stimulus; and
   means for comparing the contrast at which the person no longer perceives the visual stimulus with the contrast at which a person with normal vision no longer perceives the visual stimulus.

47. The system of claim 46 wherein said visual stimulus is displayed against a gray background.

48. The system of claim 46 wherein the contrast is reduced by a predetermined fraction of the previous value until the person no longer perceives the visual stimulus, and then is increased in predetermined incremental steps until the person again perceives the visual stimulus.

49. The system of claim 46 wherein the visual stimulus is displayed at predetermined locations within the person's visual field.

50. The system of claim 46 further including means for fixating the person's central vision.

51. The system of claim 50 wherein said means for fixating includes a fixation target.

52. The system of claim 51 wherein said fixation target is displayed at different locations within the person's visual field.

53. The system of claim 46 wherein said means for fixating includes means for monitoring the person's fixation.

54. The system of claim 46 wherein said means for displaying includes a computer.

55. The system of claim 46 further comprising means for recording the person's response to the visual stimulus.

* * * * *